(12) United States Patent
Lee

(10) Patent No.: US 8,740,862 B2
(45) Date of Patent: Jun. 3, 2014

(54) INFUSION FLOW REGULATOR, INFUSION FLOW REGULATING SET, AND INFUSION FLOW REGULATING METHOD

(75) Inventor: Doo-Yong Lee, Daejeon (KR)

(73) Assignee: Hanvit MD Co., Ltd., Daejeon (KR)

( * ) Notice: Subject to any disclaimer, the term of this patent is extended or adjusted under 35 U.S.C. 154(b) by 280 days.

(21) Appl. No.: 13/265,318

(22) PCT Filed: Aug. 31, 2011

(86) PCT No.: PCT/KR2011/006449
§ 371 (c)(1),
(2), (4) Date: Oct. 19, 2011

(87) PCT Pub. No.: WO2012/115318
PCT Pub. Date: Aug. 30, 2012

(65) Prior Publication Data
US 2012/0215181 A1 Aug. 23, 2012

(30) Foreign Application Priority Data
Feb. 23, 2011 (KR) .......................... 10-2011-0015845

(51) Int. Cl.
*A61M 5/00* (2006.01)
(52) U.S. Cl.
USPC ............ 604/250; 604/189; 604/251; 604/253

(58) Field of Classification Search
CPC ............ A61M 5/1689; A51M 5/3125; A51M 5/3126; A51M 2005/3125; A51M 2005/3126
USPC .................................. 604/189, 250, 251, 253
See application file for complete search history.

(56) References Cited

FOREIGN PATENT DOCUMENTS

| KR | 20-1999-0032991 U | 7/1999 |
|---|---|---|
| KR | 10-0706954 B1 | 4/2007 |
| KR | 20-2008-0000820 U | 5/2008 |
| KR | 10-0870440 B1 | 11/2008 |
| KR | 10-0872089 B1 | 12/2008 |

OTHER PUBLICATIONS

English Language Abstract of KR10-0706954 B1.
English Language Abstract of KR10-0870440 B1.
English Language Abstract of KR10-2008-0105910 A which is the application publication of KR10-0872089 B1.

*Primary Examiner* — Emily Schmidt
(74) *Attorney, Agent, or Firm* — Rabin & Berdo, P.C.

(57) ABSTRACT

Disclosed is an infusion flow regulator, in which a reference point is set within a manipulating range of a manipulation unit for regulating a flow rate in the infusion flow regulator, so that a manipulating point of the manipulation unit can be tuned with reference to the ratio of a flow rate measured at the reference point in relation to a prescribed injection flow rate, whereby the flow rate can be quickly and accurately tuned to the prescribed flow rate. The disclosure also includes an infusion flow regulating set including the infusion flow regulator, and an infusion flow regulating method using the same.

11 Claims, 11 Drawing Sheets

INFUSION FLOW REGULATOR, INFUSION FLOW REGULATING SET, AND INFUSION FLOW REGULATING METHOD

TECHNICAL FIELD

The present invention relates to an infusion flow regulator, in which a reference point is set within a manipulating range of a manipulation unit for regulating flow rate in the infusion flow regulator, so that a manipulating point of the manipulation unit can be tuned with reference to the ratio of a flow rate measured at the reference point in relation to a prescribed flow rate for injection, whereby the flow rate can be quickly and accurately matched to the prescribed flow rate. The present invention also relates to an infusion flow regulating set including such an infusion flow regulator, and an infusion flow regulating method using the same.

BACKGROUND ART

As shown in FIG. 1, an intravenous (IV) system for delivering an infusion solution into a vein includes: an infusion solution bottle 1, in which the infusion solution is contained; an insertion spike 11 adapted to be inserted through a sealing plug of the infusion solution bottle 1 to allow the infusion solution to be flown out from the infusion solution bottle 1; a drip chamber 12 fixed to the lower end of the insertion spike 11 so that the infusion solution can fall in drops 12a (counted in a unit of gtt) within the drip chamber 12; an injection needle 14 adapted to be inserted into a vein; a tube 13 for interconnecting the drip chamber 12 and the injection needle 14 to serve as an infusion passage for the infusion solution; and an infusion flow regulator 15 mounted in the middle of the tube 13 to be capable of regulating the flow rate of the infusion solution.

In general, the insertion spike 11, the drip chamber 12, the tube 13, the injection needle 14, and the infusion flow regulator 15 are fabricated in one set, wherein the set fabricated in this manner is referred to as an infusion set 10. After the infusion solution in the infusion solution bottle 1 connected to the infusion set 10 is completely infused to the patient, only the empty bottle 1 may be replaced by a new one containing the same infusion solution if it is necessary to continuously inject the infusion solution to the patient. In addition, the insertion spike 11 and the drip chamber 12 are fabricated to make each of the drops 12s of the infusion solution fall within the drip chamber 12 in the form of a water drop with a predetermined volume. For example, if they are fabricated to form 20 drops per 1 cc of the infusion solution, the volume of one drop will be ½₀ cc, and if they are fabricated to form 60 drops per 1 cc, the volume of one drop will be ⅟₆₀ cc. Therefore, if the drops' falling interval within the drip chamber 12 is measured, it is possible to calculate the flow rate of the infusion solution injected through the infusion set 10.

For injecting an infusion solution to a patient, the flow rate of the infusion solution is prescribed in consideration of the type of the infusion solution, the kinds of agents mixed in the infusion solution, the condition of the patient, and the kind of the disease of the patient, and the infusion flow regulator 15 is tuned so as to allow the infusion solution to be injected with the prescribed flow rate. Regulating the flow rate of the infusion liquid is very important since a medical accident may occur if the flow rate of the infusion solution being infused is not matched to the prescribed flow rate. Such an infusion flow regulator 15 has a manipulation unit 15a for regulating the cross-sectional area for passage of the infusion liquid through the tube 13, so that the injection flow rate of the infusion liquid can be regulated by manipulating the manipulation unit 15a.

The infusion flow regulator 15 shown in FIG. 1 is a so-called "roller clamp" type infusion regulator, in which the manipulation unit 15a is formed in a roller type. Referring to the infusion flow regulator 15 in more detail, a tube 13 is inserted through a recess 15b having opened top and bottom ends, and then the roller type manipulation unit 15a adapted to press the tube 13 is guided along an elongated slot 15c upward and downward. Since the depth of the recess 15b is gradually reduced as approaching the lower end of the groove 15b, and hence the tube 13 is pressed more and more as the roller 15a is moved more and more to the lower end of the groove 15b, the injection flow rate of the infusion liquid is regulated by measuring the flow rate at plural points while intermittently moving the manipulation unit 15a, and by stopping the movement of the roller 15a when the flow rate arrives at a desired level.

However, the infusion flow regulator 15 shown in FIG. 1 has a disadvantage in that since the flow rate should be measured while seeing the drip chamber 12 whenever the roller type manipulation unit 15a is stopped at a point, complicated measurements should be repeatedly performed, which will deteriorate the accuracy of flow rate regulation.

FIG. 2 shows an IV flow regulator type infusion flow regulator 15. The IV flow regulator type infusion flow regulator 15 is configured to regulate infusion flow rate by manipulating a manipulation unit 15a, which is adapted to be rotatable like a dial, to be matched to one of marked scales 15d, wherein the marked scales 15d are given marked numerical flow rate values 15e, respectively. As a result, the infusion flow rate can be regulated through a single manipulation of the manipulation unit 15a. More specifically, if the manipulation unit 15a is matched to one of the scales 15d, which is given a numerical flow rate value desired for infusion among the numerical flow rate values 15e, the cross-sectional area of the infusion passage (not shown) is regulated to allow the infusion solution to be infused with the flow rate corresponding to the numerical flow rate value desired for injection. Here, the numerical flow rate values 15e are those determined by hanging an infusion solution bottle up at a designated reference height when fabricating the infusion flow regulator, setting the infusion set 10, and then measuring the flow rate while being injected. As a result, it is possible to regulate the flow rate easily and conveniently by tuning the manipulation unit 15a with reference to the numerical flow rate values 15e after hanging the infusion solution bottle 1 up at the reference height.

However, the flow rate of an infusion solution injected to a patient by an intravenous injection system is determined not only on the basis of the installation height of the infusion solution bottle 1 but also on the basis of various factors, such as the viscosity of the infusion solution, the diameter of the injection needle 14, the venous pressure of the patient, the diameter and material of the tube 13, the ambient temperature, and the atmospheric pressure. Accordingly, there occurs a substantial difference between a flow rate indicated by one selected from the numerical flow rate values 15e marked on the IV flow regulator type infusion flow regulator and the flow rate practically measured in a state in which the manipulation unit 15a is matched to the selected numerical flow rate value. As a result, it is necessary to regulate the flow rate through repeated measurements of the flow rate like the roller clamp type infusion flow regulator even after the manipulation unit 15e is manipulated and accurately matched to the corresponding one of the numerical values 15e.

A problem herein may occur when a person responsible for regulating the flow rate of an infusion solution in accordance with a prescribed order trusts the flow regulation capability of such an infusion flow regulator after the infusion set is installed despite of the disadvantage of such an infusion flow regulator as described above. In such a case, the person may misjudge that the infusion flow regulator has been tuned to the prescribed flow rate, which may in turn cause a medical accident. On the other hand, the person may confirm that the infusion flow regulator has not been tuned to the prescribed flow rate by measuring the flow rate for the purpose of confirmation after the person manipulated the manipulation unit to match the manipulation unit to one of the numerical flow rate values 15e that corresponds to the prescribed flow rate. In such a case, however, since a required amount of moving the manipulation unit is not known, the person may repeatedly measure flow rate while intermittently moving the manipulation unit little by little, and then may tune the manipulation unit to a measurement point at which the measured flow rate somewhat corresponds to the prescribed flow rate, or to a point guessed among the repeatedly measured plural points. Following this procedure, the person may consider that the flow rate is correctly tuned. In such a case, a problem may occur due to inaccuracy in measuring flow rate in the process of repeatedly measuring the flow rate. Moreover, such inaccurate tuning of the flow rate makes it difficult to correctly determine when the infusion solution contained in the infusion solution bottle is completely consumed. As a result, the infusion set may not be timely separated from the patient at the time when the infusion solution is completely consumed, or the emptied liquid solution bottle may not be replaced by a new one, which may in turn cause a medical accident.

Therefore, such an infusion flow regulator, which is employed as a means for regulating flow rate when an infusion solution is delivered to a patient, should be fabricated to accurately regulate flow rate by reflecting all the various factors, such as the viscosity of the infusion solution, the diameter of the injection needle 14, the venous pressure of a patient, the diameter and material of the tube, the ambient temperature, and the atmosphere pressure at the time of practically using the infusion flow regulator, without relying on incorrect numerical flow rate values which do not conform to a condition at the time of practically using the infusion flow regulator since they were presented according to a specific test condition when fabricating the infusion flow regulator. In addition, the infusion flow regulator should be fabricated to regulate flow rate through a simple manipulation without repeated measurements of flow rate.

Korean Patent No. 10-0706954 discloses an "infusion flow rate measuring device" invented by the inventor of the present application, wherein the infusion velocity measuring device can measure flow rate only if counter input is performed in accordance with a drops' falling interval. In addition, Korean Patent No. 10-0872089 discloses an "infusion assistance device" also invented by the inventor of the present application, wherein the infusion assistance device outputs sounds matching a drops' falling interval to conform to an intended target flow rate so that an infusion flow regulator can be regulated to allow drops to fall in consistence with the sounds. With the devices disclosed in the above-mentioned patents, it is possible to regulate the infusion flow rate with a simple manipulation, and to quickly measure and confirm the flow rate.

The above-mentioned devices invented by the inventor of the present application have been useful in quickly and conveniently regulating infusion flow rate while carrying the devices. However, there is a problem in that the manipulation unit 15a of the infusion flow regulator 15 should be continuously manipulated until the drops' falling interval becomes matched with that of the sounds. As a result, despite of the distinguishable advantages as compared to conventional infusion regulators in terms of quick regulation and accuracy, what is needed is to improve the above-mentioned devices to regulate the flow rate more quickly and correctly. That is, since the initial position of the manipulation unit 15a is a position for stopping the injection of the infusion solution, and the target point of the manipulation unit 15a for injecting the infusion solution with a prescribed flow rate is unknown in terms of position, the manipulation unit 15a should be slowly and intermittently manipulated until it is positioned at the unknown target point in order to tune the infusion flow generator to the desired prescribed flow rate. Moreover, since drops, which fall within the drip chamber 12, fall in an instant, it is necessary to observe drops' falling more than several times so as to confirm whether the current flow rate accurately conforms to the desired flow rate, even if it is estimated that the current flow rate almost arrives at the desired flow rate. Accordingly, what is needed is to make it possible to find a correct position for the manipulation unit 15a through a single confirmation without repeatedly confirming the correct position when it is required to move the manipulation unit 15a and the correct position is unknown.

DISCLOSURE

Technical Problem

Therefore, an object of the present invention is to provide an infusion flow regulator, an infusion flow regulating set, and an infusion flow regulating method, in which all the factors for determining a flow rate except the tuning of a manipulation unit are reflected and fixed at the initial treatment stage of a patient in an environment in which an infusion set is installed, so that flow rates at a reference point, each of which is tailored to a patient's condition and situation, can be calculated and the flow rate of an infusion solution can be regulated in accordance with a relative ratio in relation to the reference point in a predetermined functional relationship established only by the tuning of the manipulation unit, which is the only variable parameter.

Another object of the present invention is to provide an infusion flow regulator, an infusion flow regulating set, and an infusion flow regulating method, in which a manipulation unit of the infusion flow regulator can be tuned to a correct flow rate through a single manipulation without needing to repeatedly manipulating the manipulation unit.

Technical Solution

In accordance with an aspect of the present invention, there is provided an infusion flow regulator which is adapted to regulate the flow rate through a tube of an infusion set by changing the diameter of the tube by a manipulation unit 110, wherein a reference point 120 is determined within a manipulation extent of the manipulation unit 110, ratios are calculated by dividing flow rates measured at individual positions within the manipulation extent by the flow rate measured at the reference point 120, and then information related to the calculated ratios are marked as a set of numerical values 131 together with a set of scales 130.

The numerical values 131 are indicated as the values of the ratios obtained through the division.

At least two reference points 120 and 120a, which are different from each other in position, are designated within the manipulation extent of the manipulation unit 110, and at least two sets of scales 130 and 130a and numerical values 131 and 131b are marked to indicate the ratios in relation to the flow rates at the reference points 120 and 120a, respectively.

A stopper 113 is formed on the manipulation unit 110, and teeth 143 are formed on the body of the infusion flow regulator 100 at each of the positions of the reference point 120 and the scales 130, so that the stopper 113 is engaged with the teeth 143 at a corresponding position when the manipulation 110 is tuned to the reference point or any of the scales.

In accordance with another aspect of the present invention, there is provided an infusion flow regulating set for regulating the flow rate of an infusion solution using an infusion set, wherein the infusion flow regulating set includes: an infusion flow regulator 100 which is adapted to regulate the flow rate through a tube of an infusion set by changing the diameter of the tube by a manipulation unit 110, wherein a reference point 120 is determined within a manipulation extent of the manipulation unit 110, ratios are calculated by dividing flow rates measured at individual positions within the manipulation extent by the flow rate measured at the reference point 120, and then information related to the calculated ratios are marked as a set of numerical values 131 together with a set of scales 130; and a flow meter 200 which measures the flow rate of an infusion solution by counting the number of drops falling within a drip chamber of the infusion set, and calculates the ratio of an intended injection flow rate in relation to the flow rate measured at the reference point 120, whereby the manipulation unit 110 of the infusion flow regulator 100 can be moved to a scale 130 conforming to the calculated flow rate ratio to tune the flow rate to the intended injection flow rate.

The flow meter 200 includes: an input unit 210 having a counter input key 211 provided for executing counter input of the number of falling drops, and an input key provided for receiving input of an intended injection flow rate value and a drop's volume value; a flow rate information calculation unit 230 for calculating the falling interval of the drops in accordance with the counter input of the number of the drops, the flow rate in accordance with the drop's volume, and a flow rate ratio which is a ratio of the intended injection flow rate in relation to the calculated flow rate; and an output unit 220 provided for outputting the calculated flow rate ratio.

The numerical values 131 marked on the infusion flow regulator 100 together with the scales 130 are indicated as the values of the ratios of the flow rates measured at the scales 130 in relation to the flow rate measured at the reference point 120.

The scales 130 are marked in an equal interval on the infusion flow regulator 100, the numerical values 131 given to the scales 130 are indicated as values increasing in proportion to the distances to the scales from the reference point 120, respectively, and the flow meter 200 stores information for the ratios obtained by dividing the flow rates measured at the positions of the scales 130 and the numerical values 131 by the flow rate measured at the reference point 120, so that the position of a corresponding scale is outputted on the basis of the information after the flow rate ratio is calculated.

In accordance with another aspect of the present invention, there is provided an infusion flow regulating method using an infusion flow regulator 100 adapted to regulate the flow rate through a tube of an infusion set by changing the diameter of the tube by a manipulation unit 110, and a flow meter 200 adapted to measure the flow rate of an infusion solution by counting the number of drops falling within a drip chamber of the infusion set, the infusion flow regulator 100 having a reference point 120 which is determined within a manipulation extent of the manipulation unit 110, and a set of numerical values 131 marked together with a set of scales 130, the numerical values 131 being marked to correspond to information related to ratios that are calculated by dividing the flow rates measured at individual positions within the manipulation extent by the flow rate measured at the reference point 120, the infusion flow regulating method including the steps of: receiving, by the infusion flow regulator 100, input of an intended injection flow rate of an infusion solution (S10); tuning the manipulation unit 110 on the infusion flow regulator 100 to the reference point 120 (S20); measuring the flow rate of the infusion solution by the flow meter 200 (S30); acquiring a target flow rate ratio by dividing the intended injection flow rate by the measured flow rate (S40); and tuning the manipulation unit 110 to one of the scales 130 corresponding to the target flow rate ratio (S50).

Advantageous Effects

According to the present invention, among various factors for determining a flow rate at an initial treatment stage, only the tuning of the manipulation unit is a variable parameter, and all the other factors are reflected and fixed at the initial stage of the treatment. As a result, specific flow rates at the reference point, each of which is tailored to a patient's condition and situation, can be calculated, and flow rate can be tuned through a single tuning of the manipulation unit in accordance with a relative flow rate ratio in relation to the reference point in a predetermined functional relationship established only by the tuning of the manipulation unit, which is the only variable parameter. Consequently, the flow rate can be quickly and accurately regulated through a single tuning of the manipulation unit without being affected by other variable factors.

In accordance with the present invention, a single measurement of flow rate at the reference point is sufficient for regulating the flow rate without needing to repeatedly measure the flow rate. As a result, the inventive infusion regulator allows quicker flow regulation as compared to a conventional infusion flow regulator, of which flow rate must be measured repeatedly while moving a manipulation unit for flow regulation.

As a result, the present invention can prevent a medical accident which has occurred due to inaccurate flow regulation caused by a conventional infusion flow regulator, on which flow rate values are indicated as absolute values although the flow rate is affected by the installation environment of the infusion flow regulator. In addition, the present invention can prevent time delay and measurement error which have been caused in the prior art due to the necessity of repeatedly measuring flow rate whenever the conventional infusion flow regulator is manipulated. Moreover, since the inventive infusion flow regulator can be easily used by a beginner or an un-skilled person, the delivery of an infusion solution can be performed more efficiently.

<Description of reference numbers>

Figure 1:
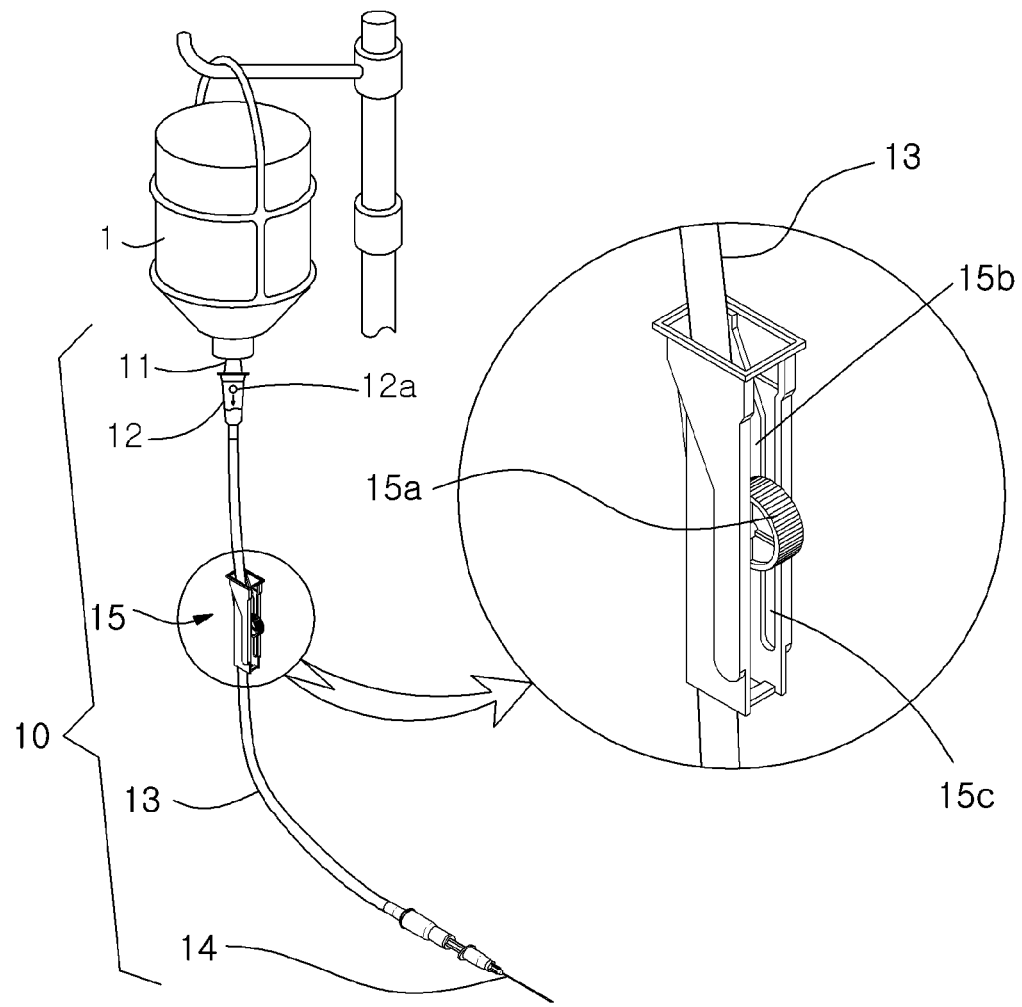
FIG. 1 schematically shows an installed condition of a conventional infusion set, and an infusion flow regulator mounted on the infusion set.

| | | |
|---|---|---|
| 200: Flow meter, | 210: Input unit, | 211: Counter input key, |
| 212: Designation key, | 213: Set key, | 220: Output unit, |
| 230: Flow rate information calculation unit, | 231: Flow rate calculation unit, | |
| 232: Flow rate ratio calculation unit, | 240: Memory | |

BEST MODE FOR CARRYING OUT THE INVENTION

Hereinafter, exemplary embodiments of the present invention will be described with reference to the accompanying drawings. In the following description and drawings, the same reference numerals are used to designate the same or similar components or functions. Further, in the following description of the present invention, a detailed description of known functions and configurations incorporated herein will be omitted when it may make the subject matter of the present invention rather unclear.

Infusion Flow Regulator

Figure 3:
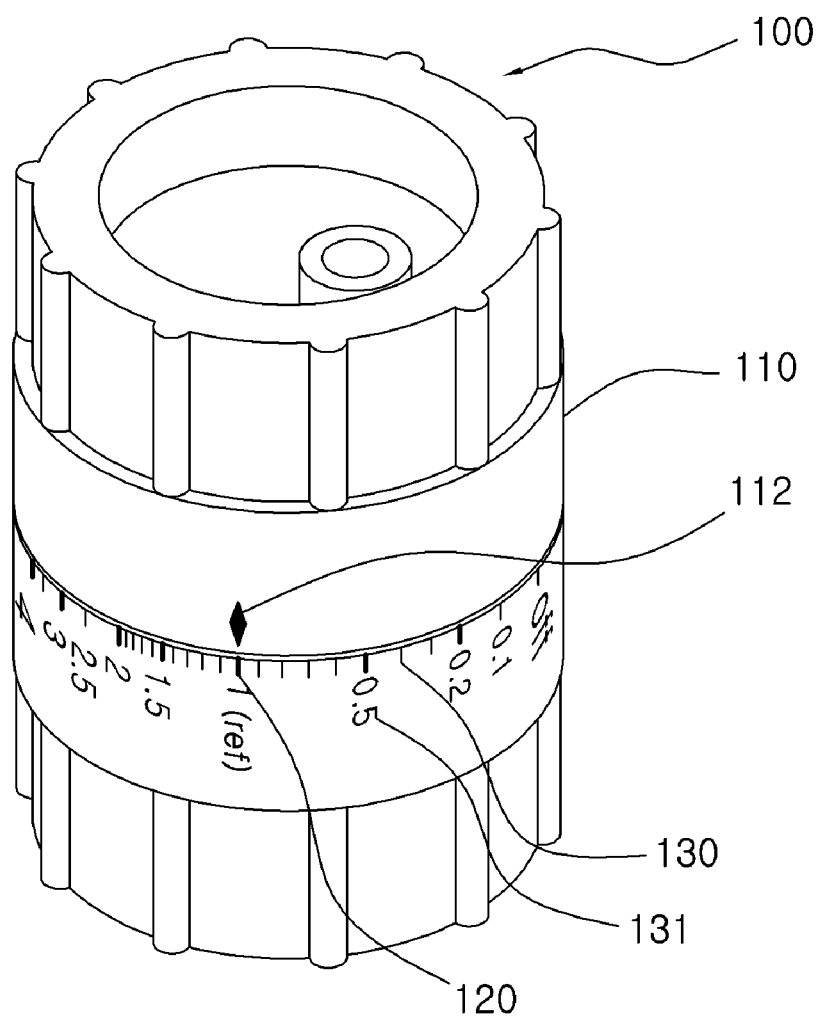
FIG. 3 is a perspective view showing an infusion flow regulator in accordance with a first embodiment of the present invention.

FIG. 3 shows an infusion flow regulator 100 in accordance with a first embodiment of the present invention, in which the present invention is applied to an IV flow regulator type infusion flow regulator.

Figure 2:
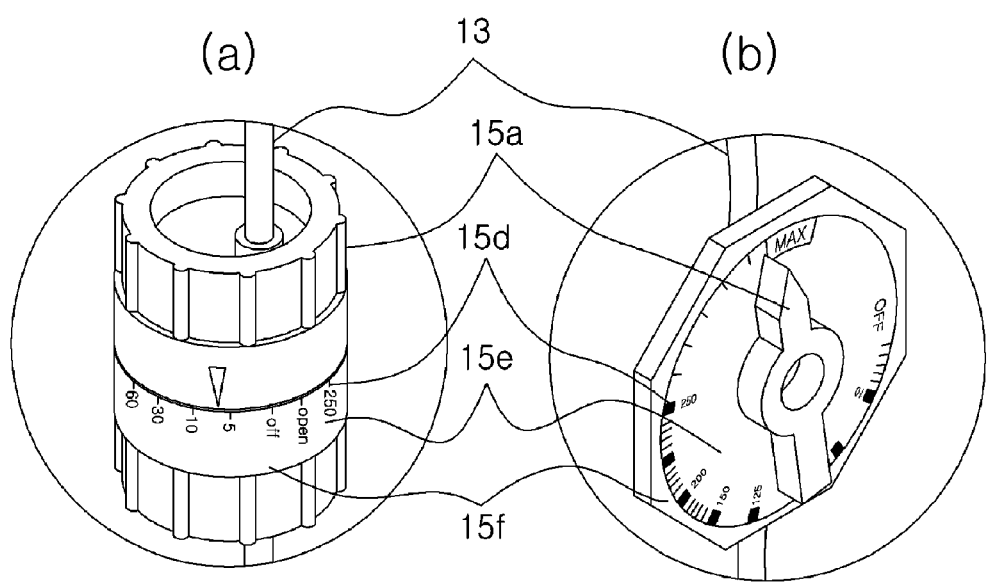
FIGS. 2a and 2b are perspective views showing other types of conventional infusion flow regulators, respectively.

Briefly describing an IV flow regulator type infusion flow regulator, which is well-known in the art, it includes a manipulation unit 110 rotatably mounted on the body 140 of the regulator, and a tube connected to the manipulation unit 110 and the body 140 at opposite ends thereof, so that an infusion solution is allowed to pass between the ends of the tube, wherein the flow rate of the infusion solution can be regulated in accordance with the rotated angle of the manipulation unit 110. Since such an IV flow regulator type infusion flow regulator is not limited to the type shown in FIG. 3, and can be fabricated in various types including that shown in FIG. 2b, it shall be noted that the embodiments of the present invention described below can be applied to any of various IV flow regulator type infusion flow regulators.

Referring to FIG. 3, there is shown an infusion flow regulator 100 having a substantially cylindrical body 140 and a manipulation unit 110 mounted on the top of the body 140, in which an indication 112 for showing the rotated extent of the manipulation unit 110 is marked on the circumferential surface of the manipulation unit 110, and a set of scales 130 and a set of numerical values 131 are marked within the rotatable extent of the indication 112, wherein the rotatable extent corresponds to the rotatable extent of the manipulation unit 110. Here, the marked scales 130 are indicated with reference to a reference point 120 which is designated within the rotatable extent of the manipulation unit 110, and the numerical values 130 given to the scales 130 are ratios of flow rates measured at the scales 130 in relation to a flow rate measured at the reference point 120, respectively. Here, the flow rate means the amount of the infusion solution to be injected per unit time (hour), which is typically indicated as the unit of cc/hr, and a flow rate prescribed to a patient by a physician is also indicated as the unit of cc/hr.

Therefore, the position of each of the scales 130, which is determined by the corresponding one of the marked numerical values 131, corresponds to a flow rate ratio obtained by Equation (1) as defined below.

(Flow rate ratio)=(Flow rate measured at a scale)÷ (Flow rate measured at a reference point)     (1)

As shown in FIG. 3, since the area allowed for marking the scales 130 and the numerical values 131 are limited and it is difficult to mark the scales 130 separately in detail, the scales are preferably marked in such a manner that they are spaced with a scale interval for allowing a user to easily observe the scales. In addition, since each of the numerical values 131 occupies a large area as compared to a corresponding scale, the number of the marked numerical values is preferably smaller than that of the scales. In other words, the scales consist of main scales, each of which is given a numerical value 131, and auxiliary scales, which are not given numerical values, wherein the auxiliary scales are marked in an interval to proportionally indicate, on the basis of the positions thereof, numerical values included between the marked numerical values for two main scales positioned before and after the auxiliary scales, respectively. In addition, the scale interval of the main scales, each of which is given a numerical value, is preferably determined in such a manner that the flow rate of an infusion solution can be included in a margin of error allowed at the time of practically prescribing the flow rate, even if the manipulation unit 110 is tuned between two main scales in consideration of the scale interval.

In addition, the infusion flow regulator 100 allows a flow rate ratio measured as described above to be obtained as a functional relationship in terms of distance from the reference point. Therefore, it is possible to determine a functional relationship showing a relation of a distance for a flow rate ratio by selecting plural points within the manipulation extent of the manipulation unit with reference to the reference point, measuring flow rates only at the selected points, and calculating flow rate ratios for the measured flow rates. As a result, a flow rate ratio at a non-selected point can also be calculated in accordance with such a functional relationship, whereby it is possible to designate the position of a scale intended to be marked.

By using the present invention configured as described above, it is possible to adjust the position for regulating a flow rate ratio by rotating the manipulation unit 110 while tuning the indication 112 with reference to the scales 130, wherein the flow rate may be gradually reduced if the manipulation unit 110 is rotated in the direction in which the marked flow rate ratios are reduced with reference to the reference point 120, the flow rate arrives at zero (0) if the indication 112 arrives at the "off" scale, and the flow rate can be gradually increased if the manipulation unit 110 is rotated in the direction in which the marked ratios are increased.

With the inventive infusion flow regulator 100 configured as described above, upon measuring the flow rate at the reference point 120, it is possible to calculate a ratio obtained by dividing a target flow rate (an intended injection flow rate) by the flow rate measured at the reference point 120, and turning the manipulation unit 110 to the scale 130 of a numerical value corresponding to the calculated ratio.

Accordingly, the inventive infusion flow regulator 100 mounted on the infusion set 10 makes it possible to know the position of the manipulation unit suitable for the prescribed flow rate of an infusion solution rendered in accordance with a physician's prescription merely by measuring the flow rate only once after the manipulation unit 110 is tuned to the reference point 120 in a state in which the infusion solution bottle 1 is hung up and the infusion set 10 is connected to the infusion solution bottle so as to inject the infusion solution to a patient. As a result, it is possible to tune the infusion flow regulator 100 in such a manner that the solution can be injected in the flow rate conforming to the prescription if the flow rate is measured only once and the manipulation unit 110 is moved only once.

Meanwhile, the reference point 120 designated within the manipulation extent of the manipulation unit 110 is preferably designated to be close to the mean value of flow rates prescribed by hospitals and clinics. Considering this, although a point, at which the flow rate is measured as 80 cc/hr under a test condition of fabricating the infusion flow regulator 100, may be determined as the reference point 120, it is possible to differently designate the reference point 120 in accordance with the types of infusion sets. The flow rate at the reference point 120 designated herein is different from the flow rate measured under the test condition due to various factors in the installation environment of the infusion flow regulator, such as the viscosity of the infusion solution at the time of practically using the infusion flow regulator, the diameter of the injection needle, the venous pressure of a patient, the diameter and material of the tube, the ambient temperature, and atmospheric pressure. However, since the flow rate ratio at each scale in relation to the flow rate at the reference point 120 is maintained even if the factors in the installation environment are changed, the flow rate can be accurately regulated by calculating the intended injection flow rate at the time of practically using the infusion flow regulator as a ratio in relation to the flow rate measured at the reference point 120, and then by tuning the flow rate in accordance with the calculated ratio, no problem will be caused even if the flow rate at the reference point 120 is different from the flow rate under the test condition.

Figure 4:
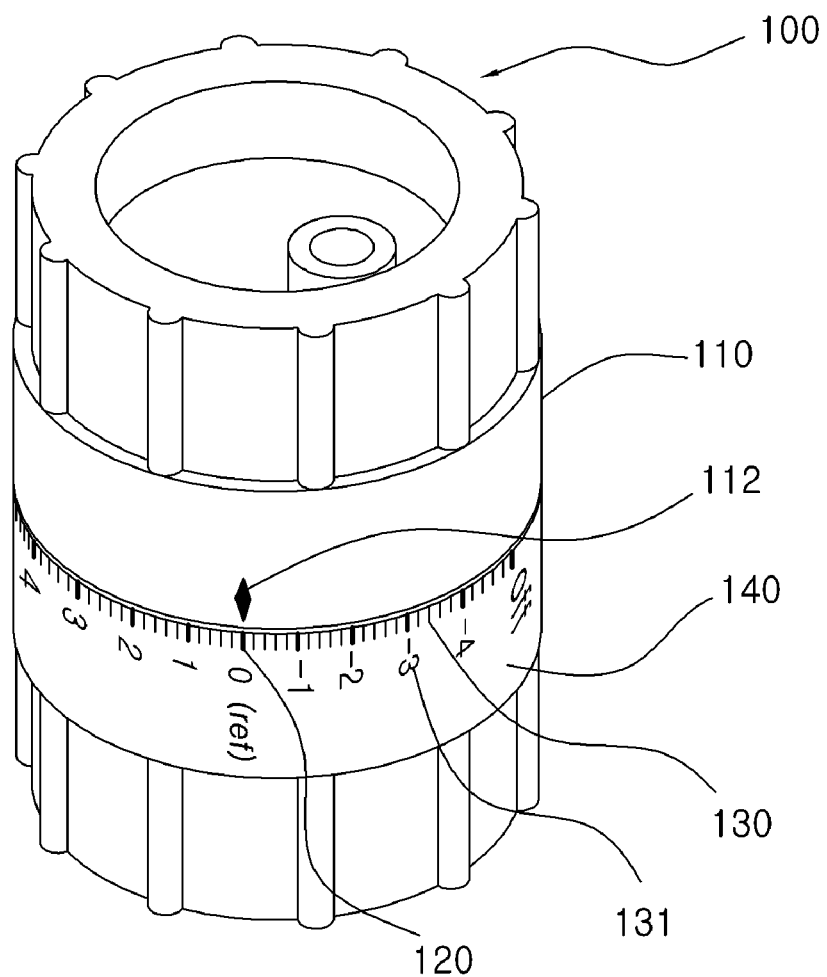
FIG. 4 is a perspective view showing an infusion flow regulator in accordance with a second embodiment of the present invention.

FIG. 4 is a perspective view of an infusion flow regulator in accordance with a second embodiment of the present invention.

Although the second embodiment shown in FIG. 4 is applied to an IV flow regulator type infusion flow regulator like the first embodiment as described above, the second embodiment is different from the first embodiment in that the scales 130 are marked in an equal scale interval with reference to the reference point 120, and the numerical values 131, which are given to some of the scales 130 due to the area occupied by the numerical values, are also marked to be proportional to the distances from the reference point 120, respectively. In other words, the scales 130 and the numerical values 131 are marked in the same method as a method of marking scales and numerical values on a measuring tape for measuring a length. The numerical values 131 in the embodiment shown in FIG. 4 are values increasing in proportion to the distances from the reference point 120, wherein the values are indicated by integers, respectively, the reference point 120 is marked as "0", and a minus symbol (−) is additionally marked to each of the numerical values marked in the direction in which the flow rate is reduced with reference to the reference point 120, so that the numerical values are contrasted with the numerical values marked in the direction in which the flow rate is increased. The numerical values 131 are not necessarily limited to positive integers, 0 and negative integers, and may be defined by various types for the purpose of the user's convenience. For example, it is possible to define plural positive integers proportional to the distances from the point "off", and to define one of the points marked with the positive integers as the reference point.

When the manipulation unit 110 is manipulated starting from the position at which the flow rate is "0" as shown in FIG. 3 (the position indicated by "off" in the drawing), a conventional and commercially available infusion flow regulator is adapted to make the flow rate increase abruptly when the manipulation unit 110 is moved in the direction in which the flow rate is increased rather than being adapted to make the flow rate increase in proportion to the manipulated extent of the manipulation unit 110. Therefore, if numerical values are determined as the ratios of flow rates measured at individual scales in relation to the flow rate measured at the reference point 120 and then scales are marked, the scale-to-scale intervals will not be equal to each other as shown in FIG. 3. Accordingly, the user may tune the manipulation unit 110 to an incorrect position when manipulating the manipulation unit 110 so as to regulate the flow rate in accordance with a calculated ratio at the time of practically injecting the infusion solution.

As such, the second embodiment of the present of the present invention forms the scales in an equal interval, and the numerical values 131 are also marked in an equal interval to be proportional to the distances as shown in FIG. 4, in which when the infusion flow regulator with the scales and numerical values formed in this manner is used, it is necessary to know in advance the information concerning the ratios corresponding to the individual scales, i.e. the ratios for the flow rates measured at the individual scales in relation to the flow rate measured at the reference point 120. The ratio values corresponding to the scales 130 can be obtained by measuring flow rate at the reference point 120 and at each of the scales 131 when fabricating the infusion flow regulator.

Figure 5:
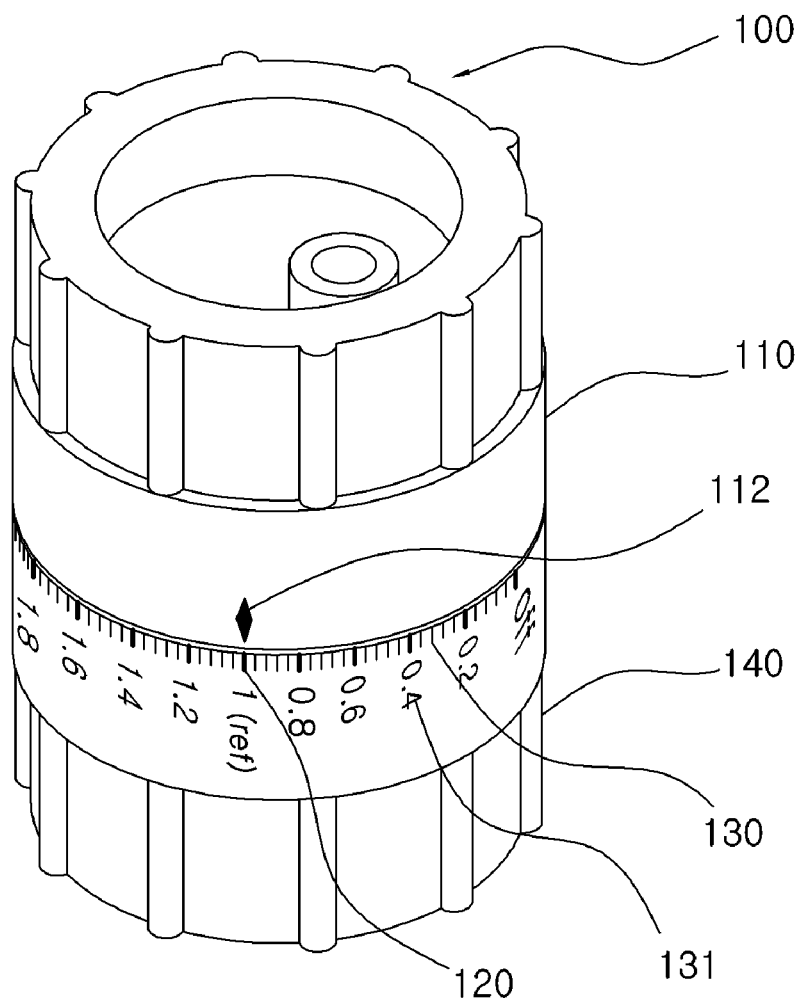
FIG. 5 is a perspective view showing an infusion flow regulator in accordance with a third embodiment of the present invention.

FIG. 5 is a perspective view of an infusion flow regulator in accordance with a third embodiment of the present invention.

Although the third embodiment is applied to an IV flow regulator type infusion flow regulator like the first and second embodiments described above, the infusion flow regulator applied in the third embodiment is different from the first and second embodiments in that it is applied to an IV flow regulator type infusion flow regulator which is fabricated to regulate flow rate in proportion to the rotated angle of the manipulation unit 110. As such, the third embodiment indicates the scales marked with reference to the reference point 120 in an equal interval, and also indicates the numerical values given to the scales as the ratios of flow rates at individual scales in relation to the flow rate at the reference point, in which the indicated numerical values are values which are increasing in proportion to the distances from the reference point, respectively.

Figure 6:
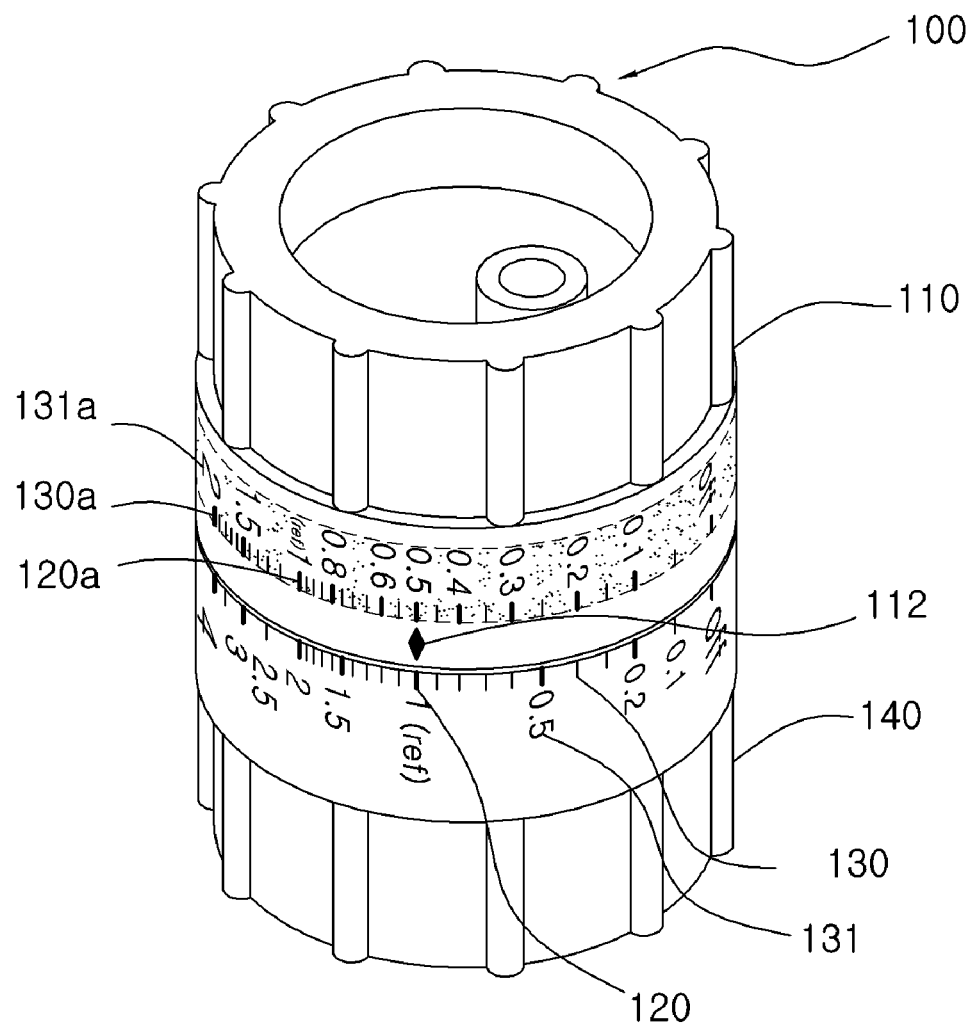
FIG. 6 is a perspective view showing an infusion flow regulator in accordance with a fourth embodiment of the present invention.

FIG. 6 is a perspective view of an infusion flow regulator in accordance with a fourth embodiment of the present invention.

The fourth embodiment of the present invention is a variant of the third embodiment as described above, wherein at least two reference points 120, at least two sets of scales 130 and at least two sets of numerical values 131 are provided. Referring to FIG. 6, one set of scales 130 are shown on the surface on which the indication 112 for indicating the present position of the manipulation unit 119 is marked, and another set of scales 130a are marked on the body 140, wherein the surface marked with the indication 112 is formed from a transparent material so that the scales 130a are visible to the outside. Here, two reference points 120 and 120a, which are designated within the rotation extent of the manipulation unit 110, are designated at different rotation angles, respectively, and two sets of numerical values 131 and 131a are marked as two sets of ratio values, respectively, wherein the two sets of ratio values are determined with reference to the reference points 120 and 120a, respectively.

By marking two sets of scales 130 and 130a, which are provided with reference to the reference points 120 and 120a of different positions, respectively, the magnitude of measured flow rate is varied depending on which reference point is used for measuring the infusion flow rate. In general, the infusion flow rate values prescribed in accordance with patients when prescribing an intended injection flow rate may be substantially different from each other. According to the present embodiment, when measuring a flow rate at a reference point to manipulate the manipulation unit 110 in accordance with the ratio of the measured flow rate to the intended injection flow rate, it is possible to measure the flow rate at the reference point having a higher flow rate value if the intended injection flow rate is high, or to measure the flow rate at the reference point having a lower flow rate value if the flow rate to be injected is low. As a result, the present embodiment can reduce the rotation angle of the manipulation unit 110 to be moved depending on a flow rate ratio.

Figure 7:
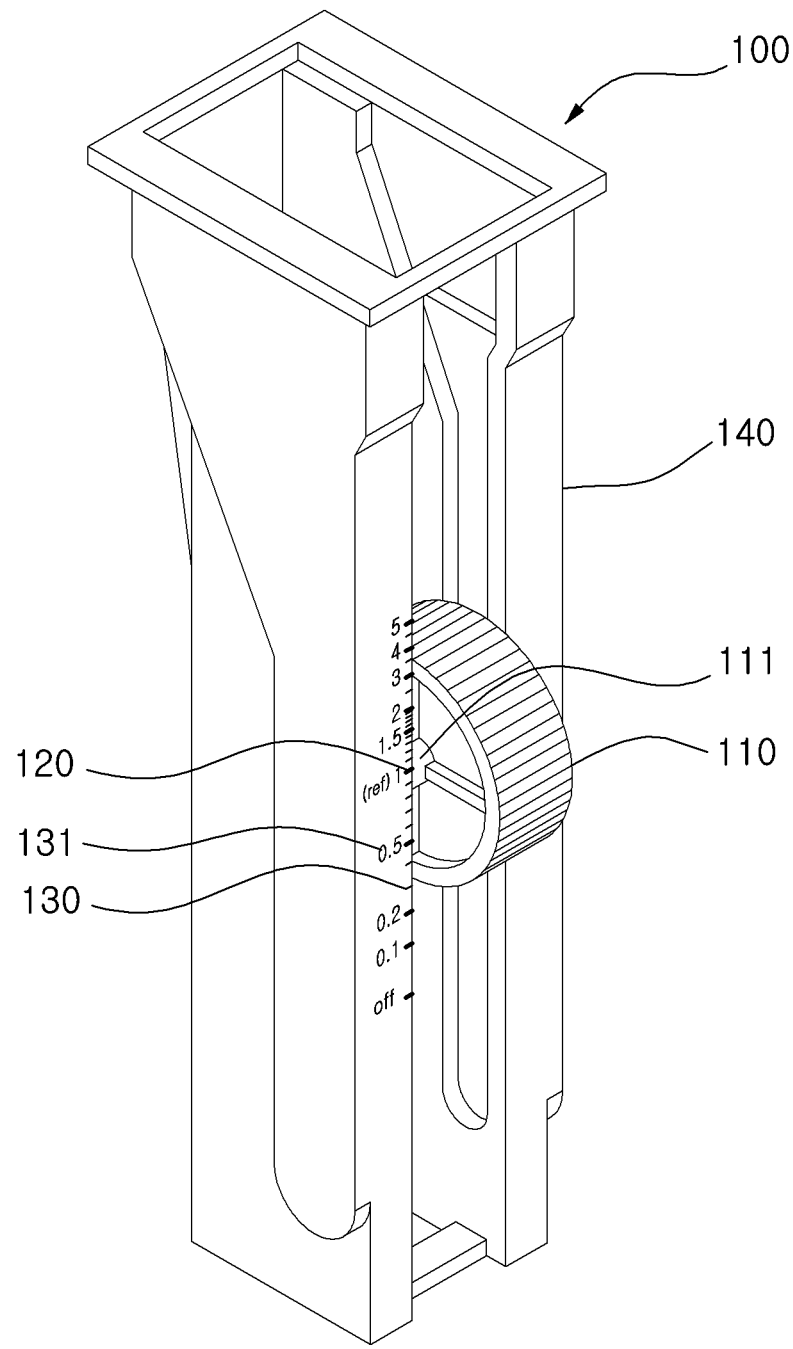
FIG. 7 is a perspective view showing an infusion flow regulator in accordance with a fifth embodiment of the present invention.

FIG. 7 is a perspective view of an infusion flow regulator 100 in accordance with a fifth embodiment of the present invention.

The infusion flow regulator 100 of the fifth embodiment is applied to a roller clamp type infusion regulator which regulates the flow rate of the infusion solution by pressing a tube 13 of an infusion set 10 by a roller type manipulation unit 110, wherein a reference point 120, a set of scales 130 and a set of numerical values 131 as described above are marked on a surface of the body 140 to correspond to the vertical movement extent of the manipulation unit 110. Since the fifth embodiment is applied to a roller clamp type infusion flow regulator in which the manipulation unit 110 is vertically moved rather than remaining stationary while being rotated, the scales 130 and the numerical values 131 are marked vertically with reference to the reference point 120. In addition, the position of the manipulation unit 110 is determined by tuning the rotation axle 111 of the manipulation unit 110 to the reference point 120 or any of the scales 130.

In addition, the above-mentioned forth embodiment, which marks two sets of scales 130 and 130a and two sets of numerical values 131 and 131a in connection with the reference points 120 and 120a of different positions, may also be applied to the roller clamp type infusion flow regulator as shown in FIG. 7 by marking a reference point 120, and a set of scales 130 and a set of numerical values 131 on one of two opposite guide faces of the roller as shown in FIG. 7, designating another reference point 120a on the other guide face, and marking another set of scales and another set of numerical values on the other guide face with reference to the reference point 120a.

Meanwhile, in the roller clamp type infusion flow regulator as shown in FIG. 7, the change of the flow rate is sensibly affected by the movement of the roller type manipulation unit 110. That is, since the manipulation unit 110 shown in FIG. 7 has a structural problem in that the flow rate is greatly changed even if the manipulation unit 110 is slightly moved, the flow rate measured at the reference point in accordance with the present invention may be incorrect, and even if the manipulation unit 110 is tuned to a scale 130 corresponding to a calculated flow rate ratio, the accuracy of the tuned position may be poor. Therefore, although it is possible to apply the inventive infusion flow regulator to a conventional roller clamp type infusion flow regulator, it is desirable to apply the inventive infusion flow regulator to an infusion flow regulator which can accurately regulate the flow rate. Therefore, in the sixth embodiment of the present invention to be described below, the present invention is applied to the infusion flow regulator which was invented by the inventor of the present invention, and is disclosed Korean Patent No. 10-0870440, so as to improve the accuracy of flow rate regulation.

Figure 8:
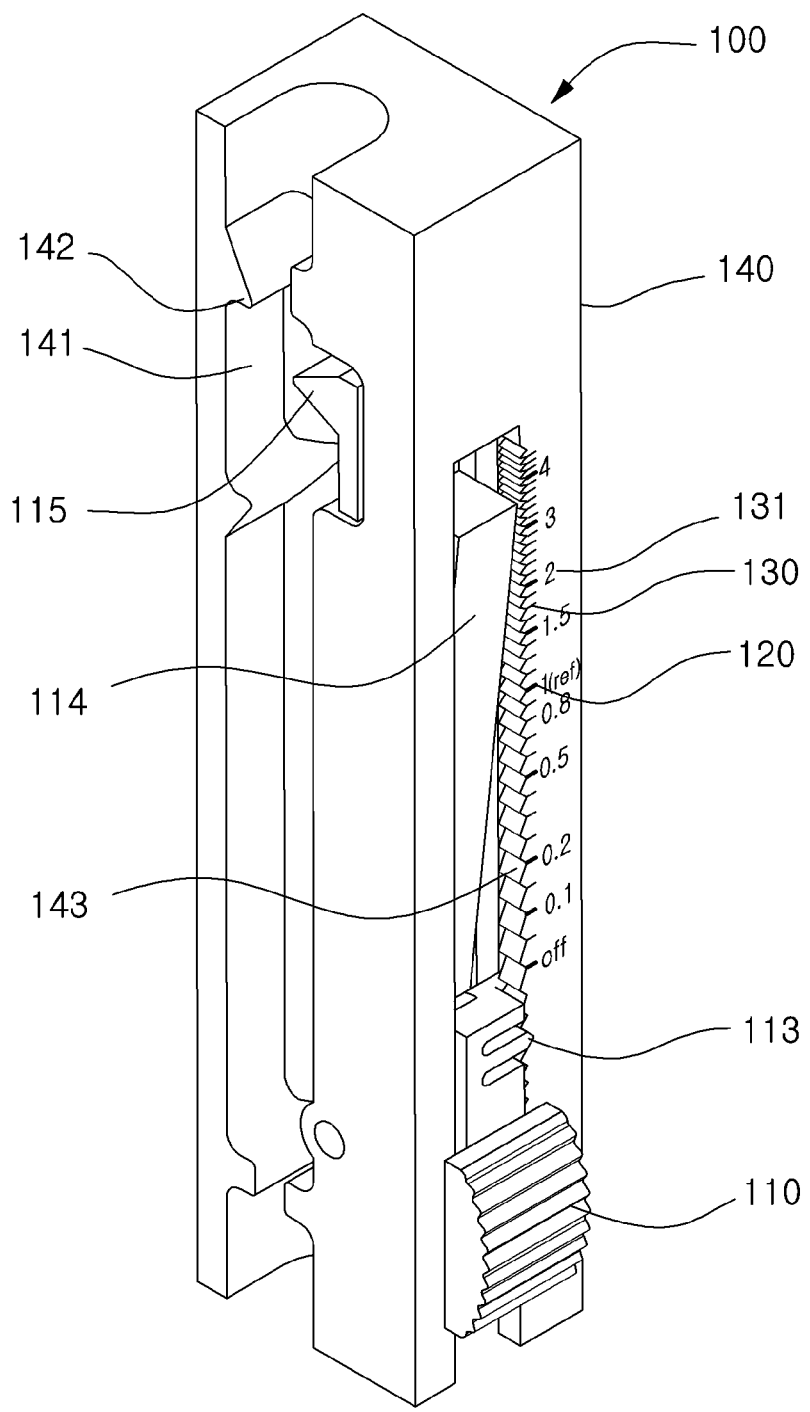
FIG. 8 is a perspective view showing an infusion flow regulator in accordance with a sixth embodiment of the present invention.

FIG. 8 is a perspective view of an infusion flow regulator in accordance with the sixth embodiment of the present invention.

The infusion flow regulator shown in FIG. 8 is configured as follows: a bending protrusion 142 is formed in a tube passage groove 141 of the body 140 of the regulator, the tube passage groove 141 allowing the tube to extend vertically through the groove 141; a press protrusion 115, which is formed on a tube press unit 114 mounted to be rotatable in the body, presses the tube in the opposite side to the bending protrusion 142 to bend the tube; and a manipulation unit 110, which is slid along the body 140, regulates the pressed extent of the tube press unit 114 in accordance with the moved position of the manipulation unit 110. The infusion flow regulator has an advantage in that it is not necessary to apply an excessive force and the flow rate can be regulated accurately since the flow rate is regulated not only by pressing the tube but also on the basis of the bent extent of the tube. In the present embodiment, the present invention can be applied in such a manner that a reference point 120, scales 130 and numerical values 131 are marked on the surface of the body 140 within the moving extent of the manipulation unit 110 as in the fifth embodiment described above.

Referring to FIG. 8, teeth 143 are continuously formed on a wall of an elongated slit, which is formed in the body 140, the manipulation unit 110 being moved along the slit, and a stopper 113 is formed on the manipulation unit 110 to be engaged with the teeth. As a result, the stopper 113 is moved whenever the manipulation unit 110 is moved, and is stopped at a position where the manipulation unit 113 is stopped by being engaged with the teeth 143 at the position. As a result, the manipulation unit 10 remains stationary at the stopped position without being moved unless an external force is applied to the manipulation unit 110, which makes it possible to stably inject an infusion solution with a tuned flow rate without the change of flow rate. In the present embodiment, the valleys of the teeth 143 accurately conform to the positions of the reference point 120 and the scales 130, respectively. That is, in accordance with the present invention, when the infusion flow rate is at the reference point 120, the manipulation unit 110 can be accurately tuned to the reference point 120, and when the manipulation unit 110 is tuned to a scale corresponding to a calculated flow rate ratio, the manipulation unit can be accurately tuned to the corresponding scale. With this configuration of the present invention, the manipulation unit 110 cannot be positioned between two adjacent valleys. As a result, it is desirable that the valley-to-valley interval is determined within an allowable error range.

The teeth 143 formed to correspond to the reference point 120 and the scales 130 may also be applied to the first to fourth embodiments described above. Since the first to fourth embodiments are different from the sixth embodiment only in that they are applied to an IV flow regulator type infusion flow regulator and the manipulation unit 110 is rotated in the first to fourth embodiments, the teeth 143 may be formed along the circumference of the body within the rotation extent of the manipulation unit 110 in such a manner that one valley is formed at a position corresponding to each of the reference point 120 and the scales 130. In such a case, a stopper 113 may be formed on the manipulation unit 110. Since such a modification can be made by a person skilled in the art in accordance with the shape of an IV flow regulator type infusion flow regulator with reference to the sixth embodiment, such a modification is not shown in the accompanying drawings.

Infusion Flow Regulating Set and Method

Figure 9:
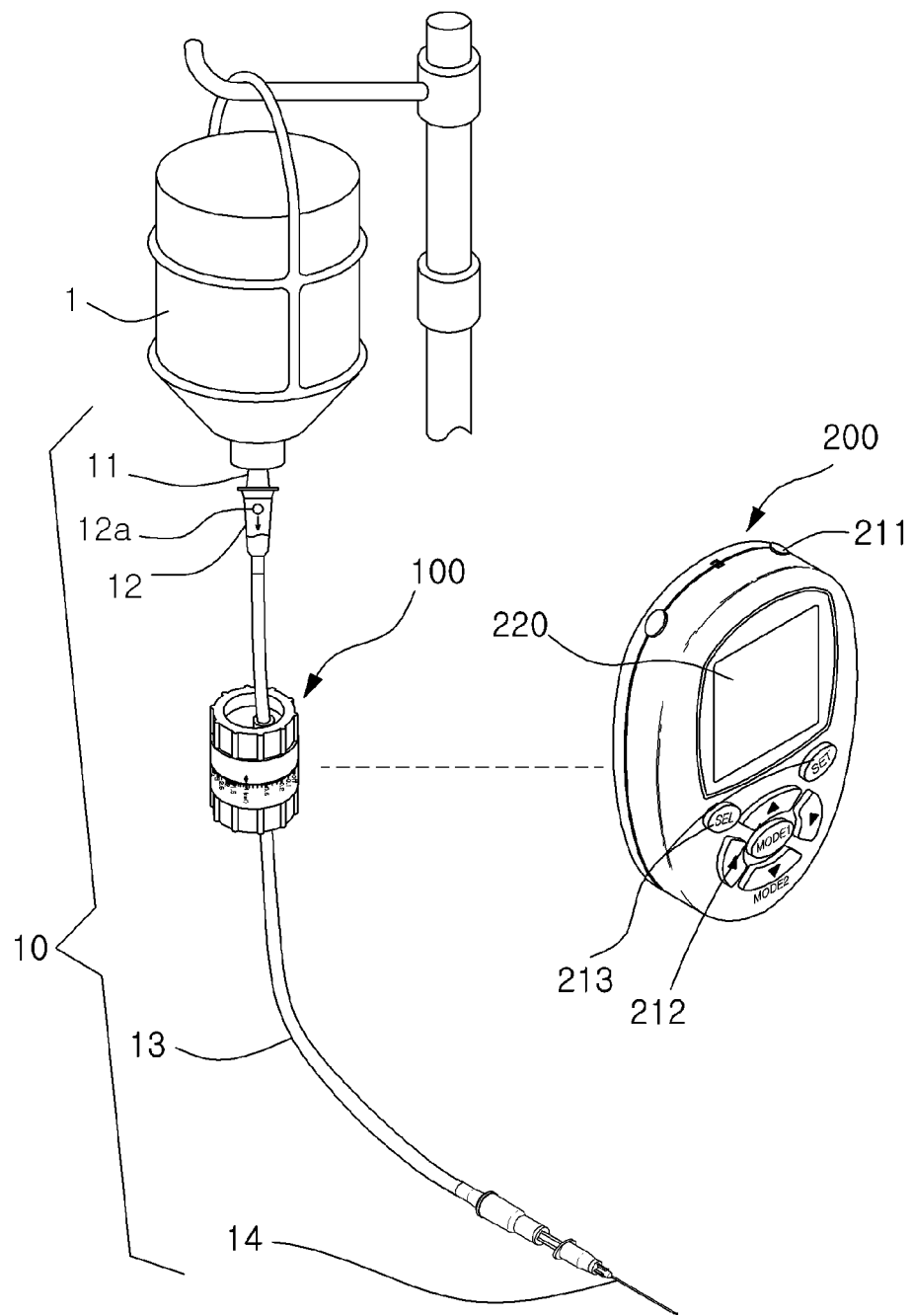
FIG. 9 exemplifies a use of an infusion flow regulating set in accordance with an embodiment of the present invention.
Figure 10:
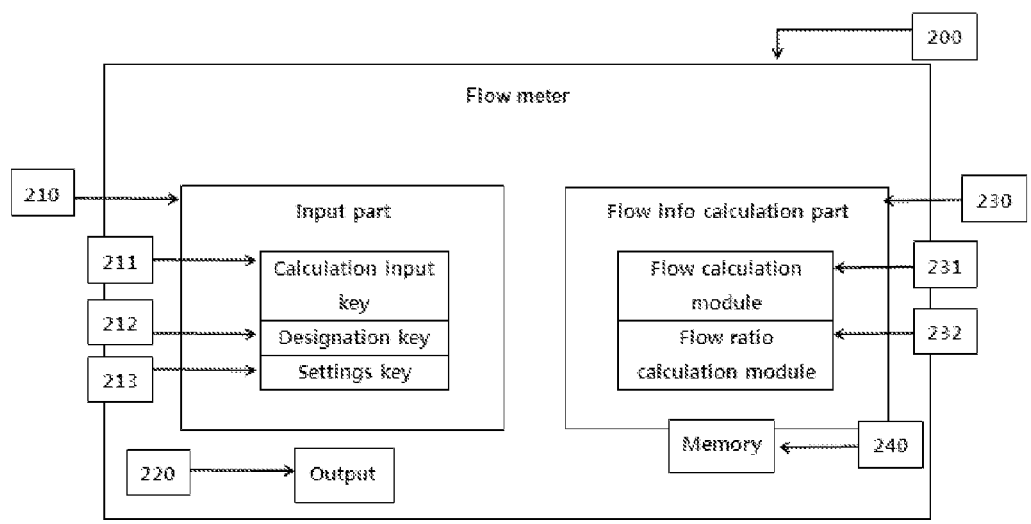
FIG. 10 is a block diagram of the flow rate measuring instrument 200 in the infusion flow regulating set.
Figure 11:
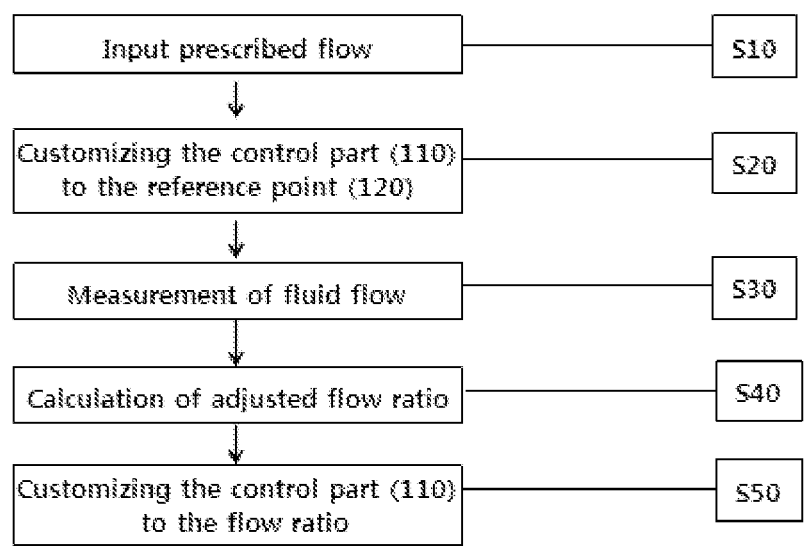
FIG. 11 is a flowchart of an infusion flow regulating method in accordance with an embodiment of the present invention.

FIG. 9 exemplifies a use of the inventive infusion flow regulating set, FIG. 10 is a block diagram of a flow meter in the inventive infusion flow regulating set, and FIG. 11 is a flowchart of the inventive infusion flow regulating method.

The inventive infusion flow regulating set includes an infusion regulator 100 as described above, and a flow meter 200 for measuring infusion flow rate. Since the infusion flow regulator 100 was described in the first to sixth embodiments, it will not be described any more, and the present embodiment regarding an infusion flow regulating set will be described with reference to a case in which the infusion flow regulator 100 in accordance with the second embodiment is employed, although the infusion flow regulators of the first, third, fourth and fifth embodiments can be employed in the present embodiment.

The flow meter 200 is configured to measure the flow rate of an infusion solution to be injected by counting the number of drops 12a falling down within the drip chamber 12 of the infusion set 10 in consistence with the drops' falling time, and to calculate the ratio of a measured flow rate in relation to an intended injection flow rate (prescribed flow rate).

More specifically, the flow meter 200 includes: an input unit 210 receiving input from a user; an output unit 220 for visually outputting various situation data; a flow rate information calculation unit 230 for calculating a flow rate in accordance with the input of the input unit 210, calculating a flow rate ratio in accordance with the calculated flow rate and outputting the calculated flow rate ratio to the output unit 220; and a memory 240 for storing various programs required for calculating the flow rate and flow rate ratio to provide the program information when the flow rate information calculation unit 230 is operated.

The input unit 210 includes: counter input keys 211 provided to execute counter input of drops falling within the drip chamber 12 at the drops' falling time; and designation keys 212 and setting keys 213 provided to allow a user to input information required for operating the present invention. Here, the designation keys 212 are used for selecting and inputting a flow rate of an infusion solution determined in accordance with a physician's prescription (for example, a flow rate input in the unit of cc/hr), and for selecting a volume of one drop 12b determined in accordance with the fabricated construction of the infusion set 10 (for example, 1/20 cc/gtt, 1/60 cc/gtt, 1/10 cc/gtt, 1/15 cc/gtt and 1/30 cc/gtt), and the setting keys are used for operating the flow rate information calculation unit 230 after the input of the values selected by the designation keys 212 is completed. Meanwhile, in connection with the flow rate of the infusion solution to be injected, the total amount (cc) of the infusion solution and the total length of time (hr) to be consumed to inject the infusion solution completely may be selected using the designation keys 212, in which case the flow rate information calculation unit 230 calculates the flow rate (cc/hr) of the infusion solution to be injected by dividing the total amount of the infusion solution by the total length of time. The combination of the designation keys 212 and the setting keys 213 for selecting and/or inputting required information is not limited to that shown in FIG. 9 and may be formed using various types of input keys known in the art.

The flow rate information calculation unit 230 includes a flow rate calculation module 231 for calculating a flow rate, and a flow rate calculation module (232) for calculating a flow rate ratio in accordance with a flow rate (prescribed flow rate) value of the infusion solution to be injected, which is input through the input unit 210.

The flow rate calculation module 231 continuously receives counter input executed plural times through the counter input keys to calculate the number of drops per unit hour (gtt/hr) in accordance with the times of executing the counter input, and the length of time consumed for executing the counter input, multiplies the calculated number of drops per unit hour by the volume of one drop to calculate the flow rate (cc/hr) of the infusion solution as being currently injected, and outputs the flow rate of the infusion solution to the output unit 220. The flow rate calculation module 231 may be preferably configured by employing the flow rate measuring unit disclosed in Korean Patent No. 10-0706954 entitled, "Device for Measuring Infusion Solution Injection Velocity," which was invented by the present inventor, in which the number of drops per unit hour is calculated at the time when counter input is received by a preset number of times, and if the counter input is received beyond the preset number of times, the number of drops per unit hour is calculated for the counter input which has been most recently received the preset number of times whenever the counter input is received beyond the preset number of times. In addition, it is desirable to confirm time intervals for continuously receiving counter input the preset number of times, and to calculate the flow rate only when the time intervals are within a preset range allowable in order to prevent the flow rate from being miscalculated due to any error in executing counter input.

The flow rate ratio calculation module 232 calculates a flow rate ratio by dividing an intended injection flow rate (a prescribed flow rate) by the flow rate (cc/hr) calculated by the flow rate calculation module 231, in which case the calculated flow rate ratio is also outputted through the output unit 220 so as to allow the user to tune the manipulation unit 110 of the infusion flow calculator 100 to the flow rate ratio.

An infusion flow regulating method using the infusion flow regulating set configured as described above will be described with reference to FIG. 11.

At first, a flow rate value prescribed by a physician is input to the flow meter 200, and a drop's volume is also selected and input in a state in which the infusion solution bottle 1 is hung on a stand, and the infusion set 10 formed by mounting the tube in the infusion flow regulator 100 is connected to the infusion solution bottle 1 (S10).

Next, the manipulation unit 110 of the infusion flow regulator 100 is tuned to the reference point 120 marked on the body of the infusion flow regulator 100 (S20).

Then, the infusion solution contained in the infusion solution bottle 1 falls in drops 12a within the drip chamber 12 of the infusion set 10 and is injected through the tube 13, in which case the counter input key 211 of the flow meter 200 is input whenever a drop falls so as to measure the injected flow rate of the infusion solution (S30).

Next, the flow meter 200 calculates a flow rate ratio to be tuned in relation to the reference point 120 by dividing the prescribed flow rate value by the measured flow rate value (S40). The flow rate ratio can be calculated by Equation (2) as defined below.

Flow rate ratio=(Prescribed flow rate)÷(Flow rate measured at reference point)   (2)

Next, the manipulation unit 110, which has been tuned to the reference point 120 in the infusion flow regulator 100, is tuned to a position of a scale 130 corresponding to the flow rate ratio calculated using Equation (2) to regulate the flow rate (S50).

Meanwhile, after the manipulation unit 110 is tuned to the position of the scale 130 corresponding to the flow rate ratio, it is desired to confirm whether the flow rate corresponds to the prescribed flow rate by measuring the flow rate once again using the flow meter 200. Instead of measuring the flow rate, it is possible to employ a sound outputting method disclosed in Korean Patent No. 10-0872089, entitled "Device for Assisting Injection of Infusion Solution" invented by and filed in the name of the inventor of the present application. For this purpose, the flow meter 200 may include a module (not shown) for calculating a dripping interval corresponding to a flow rate value prescribed by a physician; and a speaker (not shown) for outputting a sound in accordance with the calculated dripping interval. Here, the dripping interval (gtt/hr) is obtained by dividing the prescribed flow rate value (cc/hr) by a drop's volume (cc/gtt), and the sound is outputted after the step S50 for regulating the flow rate by the manipulation unit as described above.

In accordance with the third embodiment described above with reference to FIG. 5, the scales 130 are marked in an equal interval, and the marked numerical values 131 are increasing in proportion to the distances to the reference point 120, respectively. As a result, the flow rate ratio calculated at a position of a scale corresponding to one of the numerical values 131 is different from the corresponding numerical value 131.

Therefore, in order to configure an infusion flow regulating set by combining the infusion flow regulator 100 according to the third embodiment and the flow meter 200, it is necessary to additionally store, in the memory 240, a data table which associates the flow rate ratio values at the positions of the scales 130 given the numerical values 131 with the scales 130 and the numerical values 131, respectively, so that the flow rate ratio calculation unit 232 can read a numerical value corresponding to a calculated flow rate ratio from the datable and can output, through the output unit 220, the numerical value read from the data table rather than the calculated flow rate ratio. Meanwhile, if auxiliary scales, which are not given numerical values, are marked on the infusion flow regulator 100, the auxiliary scales are also marked in an equal interval, in which case the numerical values corresponding to the auxiliary scales should also be added to the data table.

Although the embodiment described above employs a data table for associating the numerical values 131 marked on the infusion flow regulator 100 with practical flow rate ratios, it is possible to derive an equation correlated to the numerical values 131 and the practical flow rate ratios, and to substitute a calculated flow rate ratio to the correlated equation to obtain a corresponding numerical value

INDUSTRIAL APPLICABILITY

Although several exemplary embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. An infusion flow regulator, comprising:
   a manipulation unit regulating a flow rate of an infusion solution flowing through a tube by changing a diameter of the tube;
   a body mounting the manipulation unit;
   a reference point marked on a surface of the body;
   a set of scales marked on the surface of the body, each scale of the set of scales having an interval from the reference point in proportion to a flow rate ratio of said each scale, the flow rate ratio being calculated by dividing the flow rates rate of the infusion solution measured at each scale by a reference flow rate measured at the reference point; and
   a set of numerical values marked on the surface of the body, each numerical value of the set of numerical values corresponding to said each scale.

2. The infusion flow regulator as claimed in claim 1, wherein said each numerical value indicates the flow rate ratio of each corresponding scale.

3. The infusion flow regulator as claimed in claim 2, further comprising:
   a second reference point marked in a different position from the reference point;
   a second set of scales, each scale of the second set of scales having an interval from the second reference point in proportion to a second flow rate ratio of said each scale of the second set of scales; and
   a second set of numerical values, each numerical value of the second set of numerical values corresponding to said each scale of the second set of scales and indicating the second flow rate ratio of each corresponding scale.

4. The infusion flow regulator as claimed in claim 2, further comprising:
   a stopper formed on the manipulation unit; and
   a plurality of teeth formed on the body,
   wherein the stopper is engaged with one of the teeth.

5. An infusion flow regulating set comprising:
   an infusion flow regulator including
      a manipulation unit regulating a flow rate of an infusion solution flowing through a tube by changing a diameter of the tube,
      a body mounting the manipulation unit;
      a reference point marked on a surface of the body;
      a set of scales marked on the surface of the body, each scale of the set of scales having an interval from the reference point in proportion to a flow rate ratio of said each scale, the flow rate ratio being calculated by dividing the flow rate of the infusion solution measured at said each scale by a reference flow rate measured at the reference point; and
      a set of numerical values marked on the surface of the body, each numerical value of the set of numerical values corresponding to said each of the scales; and
   a flow meter measuring the reference flow rate by counting a number of falling drops at the reference point, and calculating the flow rate ratio of an intended injection flow rate inputted by a user to the reference flow rate measured by the flow meter.

6. The infusion flow regulating set as claimed in claim 5, wherein the flow meter comprises:
an input unit including
a counter input key executing a counter input of the number of falling drops, and
a designation key receiving the intended injection flow rate and a drop's volume value of the falling drops;
a flow rate calculation unit calculating
a falling interval of the falling drops using the counter input of the number of the falling drops,
the reference flow rate using the falling interval and the drop's volume value of the falling drops, and
the flow rate ratio of the intended injection flow rate to the reference flow rate; and
an output unit outputting the calculated flow rate-ratio.

7. The infusion flow regulating set as claimed in claim 5, wherein said each numerical value indicates the flow rate ratio of the flow rate measured at said each scale to the reference flow rate measured at the reference point.

8. The infusion flow regulating set as claimed in claim 6, wherein the flow meter stores information of the flow rate ratio of said each scale, and outputs the calculated flow rate ratio of the intended injection flow rate as a corresponding scale of the set of scales.

9. An infusion flow regulating method comprising:
receiving, by a flow meter, a value of an intended injection flow rate of an infusion solution;
tuning a manipulation unit of an infusion flow regulator to point at a reference point;
measuring, by the flow meter, a reference flow rate of the infusion solution at the reference point;
calculating a flow rate ratio by dividing the intended injection flow rate by the reference flow rate; and
tuning the manipulation unit to point at one of the scales corresponding to the flow rate ratio,
wherein the infusion flow regulator including
the manipulation unit regulating a flow rate of the infusion solution flowing through a tube by changing a diameter of the tube,
a body mounting the manipulation unit,
a reference point marked on a surface of the body;
the scales marked on the surface of the body, each of the scales having an interval from the reference point in proportion to the flow rate ratio of said each scale, and
numerical values marked on the surface of the body, each of the numerical values corresponding to said each scale, and
wherein the flow meter measures the reference flow rate by counting a number of falling drops at the reference point.

10. The infusion flow regulator as claimed in claim 3, further comprising:
a stopper formed on the manipulation unit; and
a plurality of teeth formed on the body,
wherein the stopper is engaged with one of the teeth.

11. The infusion flow regulator as claimed in claim 1, further comprising:
an indication marked on a surface of the manipulation unit and indicating a relative position of the manipulation unit to the set of scales.

* * * * *